United States Patent
King

(10) Patent No.: US 7,348,573 B2
(45) Date of Patent: *Mar. 25, 2008

(54) EXCITATION AND EMISSION FILTER

(75) Inventor: Howard G. King, Berkeley, CA (US)

(73) Assignee: Applera Corporation, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/531,548

(22) Filed: Sep. 13, 2006

(65) Prior Publication Data

US 2007/0008537 A1   Jan. 11, 2007

Related U.S. Application Data

(63) Continuation of application No. 10/735,339, filed on Dec. 12, 2003, now Pat. No. 7,119,345.

(60) Provisional application No. 60/450,734, filed on Feb. 28, 2003.

(51) Int. Cl.
*G01N 21/64* (2006.01)

(52) U.S. Cl. .................................... 250/458.1

(58) Field of Classification Search ............. 250/458.1, 250/459.1, 461.1, 461.2
See application file for complete search history.

(56) References Cited

U.S. PATENT DOCUMENTS

| | | | |
|---|---|---|---|
| 3,811,777 A | 5/1974 | Chance | |
| 5,157,262 A | 10/1992 | Marsoner et al. | |
| 5,757,014 A | 5/1998 | Bruno et al. | |
| 5,854,684 A | 12/1998 | Stabile | |
| 6,432,634 B1 * | 8/2002 | Digby et al. ................... | 435/6 |
| 6,603,126 B2 | 8/2003 | Yamada et al. | |
| 2003/0030804 A1 | 2/2003 | Nordman et al. | |
| 2003/0160957 A1 | 8/2003 | Oldham et al. | |

FOREIGN PATENT DOCUMENTS

| | | |
|---|---|---|
| EP | 0854362 | 7/1998 |
| WO | 03/098278 | 11/2003 |
| WO | 03/098279 | 11/2003 |

* cited by examiner

*Primary Examiner*—Constantine Hannaher

(57) ABSTRACT

Systems and methods for detecting fluorescent light by providing a filter assembly including an excitation filter and an emission filter.

28 Claims, 13 Drawing Sheets

EXCITATION AND EMISSION FILTER

CROSS-REFERENCE TO RELATED APPLICATIONS

This application is a continuation of Ser. No. 10/735,339 filed Dec. 12, 2003 now U.S. Pat. No. 7,119,345, which claims a benefit from U.S. Provisional Patent Application No. 60/450,734, filed Feb. 28, 2003. Cross-reference is made to co-pending U.S. patent application Ser. Nos. 10/440,719, 10/440,852, and 10/440,920, all filed on May 19, 2003, and to co-pending U.S. patent application Ser. No. 10/216,620, filed Aug. 9, 2002, which is a continuation of co-pending U.S. patent application Ser. No. 09/700,536, filed Nov. 29, 2001, which claims priority to International Patent Application No. PCT/US99/11088, filed May 17, 1999, which published as publication number WO 99/60381. All Patents, Patent Applications, and publications mentioned herein are incorporated herein in their entireties by reference.

FIELD

The present teachings relate to systems and methods for detecting fluorescence.

BACKGROUND

Systems for detecting fluorescence can include multiple detectors to provide singular detection for each sample analyzed. These systems can include singular excitation for each sample analyzed. These systems can include multiple excitation for each sample analyzed. These systems can include filters to separate the excitation wavelengths from the emission wavelengths. It can be desirable to include filters to provide both excitation filtering and emission filtering.

SUMMARY

According to various embodiments, the present teachings can provide a fluorescent detection system including an array of excitation light sources, an array of detectors, and a filter assembly including an excitation filter positioned for excitation light from the excitation light sources and an emission filter positioned for fluorescent light from an array of samples, wherein the excitation filter and emission filter are positioned substantially parallel to each other.

According to various embodiments, the present teachings can provide a filter assembly including an excitation filter adapted to condition excitation light from an excitation light source, and an emission filter adapted to condition fluorescent light from a sample, wherein the excitation filter and the emission filter are form alternating portions of the filter assembly, wherein the filter assembly is substantially flat.

According to various embodiments, the present teachings can provide a method of fluorescent detection including providing a flat filter assembly including an excitation filter, and an emission filter, providing excitation light, positioning the excitation light to correspond with the excitation filter, conditioning the excitation light with the excitation filter, providing a sample adapted to generate fluorescent light when excited by the excitation light, positioning the fluorescent light to correspond with the emission filter, conditioning the fluorescent light with the emission filter, detecting the conditioned fluorescent light.

Additional embodiments are set forth in part in the description that follows, and in part will be apparent from the description, or may be learned by practice of the various embodiments described herein.

BRIEF DESCRIPTION OF THE DRAWINGS

Various embodiments of the present teachings are exemplified in the accompanying drawings. The teachings are not limited to the embodiments depicted, and include equivalent structures and methods as set forth in the following description and known to those of ordinary skill in the art. In the drawings.

Figure 1:
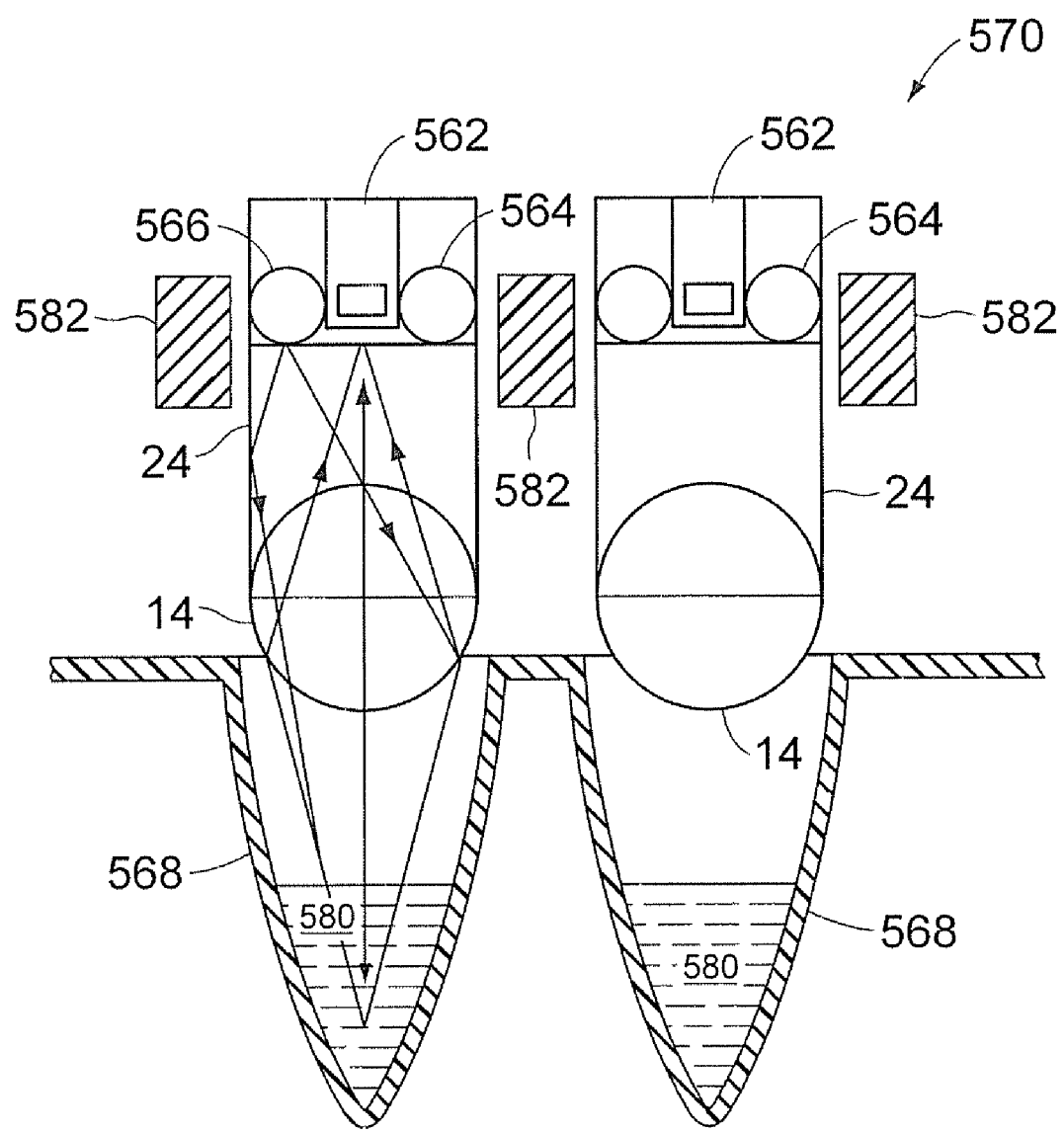
FIGS. 1-5 illustrate a side, partial cross-sectional view of a system according to various embodiments.

The ghost lines in the figures represent object in a different plane. The object in solid in the figures represent objects in a near plane that can be transparent. If transparent, than the objects drawn with ghost lines can be visible through the objects drawn in solid.

It is to be understood that both the foregoing general description and the following detailed description are exemplary and explanatory only and are intended to provide a further explanation of the various embodiments of the present teachings.

DESCRIPTION OF VARIOUS EMBODIMENTS

Reference will now be made to various exemplary embodiments, examples of which are illustrated in the accompanying drawings. Wherever possible, the same reference numbers are used in the drawings and the description to refer to the same or like parts.

The term "excitation light source" as used herein refers to a source of irradiance that can provide excitation that results in fluorescent emission. Light sources can include, but are not limited to, white light, halogen lamp, lasers, solid state laser, laser diode, micro-wire laser, diode solid state lasers (DSSL), vertical-cavity surface-emitting lasers (VC-SEL,), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, filament lamps, arc lamps, gas lamps, and fluorescent tubes. Light sources can have high irradiance, such as lasers, or low irradiance, such as LEDs. The different types of LEDs mentioned above can have a medium to high irradiance.

The term "detector" as used herein refers to any component, portion thereof, or system of components that can detect light including a charged coupled device (CCD), back-side thin-cooled CCD, front-side illuminated CCD, a CCD array, a photodiode, a photodiode array, a photomultiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

The term "filter assembly" as used herein refers to any component or combination of components that provides excitation filtering and emission filtering assembled together. A filter assembly can be assembled mechanically or chemically. A filter assembly can include separate filters or filtering regions. A substantially flat filter assembly can have a planar overall structure. In a substantially flat filter assembly, the excitation filter and emission filter can be positioned substantially parallel to each other, which refers to the filters being substantially parallel in different parallel planes or substantially parallel in substantially the same plane. A filter cube with filters on perpendicular faces is neither substantially flat nor does it have filters in parallel planes.

The term "filter" as used herein refers to any electromagnetic radiation exclusion device that can operate at a particular wavelength or range of wavelengths. Filter includes optical filters. Filter can include a shortpass filter, a longpass filter, a multi-notch filter, and/or a bandpass filter. The terms "shortpass" filter and "longpass" filter as used herein refer to relative filtering ranges on the spectrum of excitation light and emission light.

The term "sample chamber" as used herein refers to any structure that provides containment to the sample. The sample chamber can be open or transparent to provide entry to excitation light and exit to fluorescent light. The transparency can be provided glass, plastic, fused silica, etc. The sample chamber can take any shape including a well, a tube, a vial, a cuvette, a tray, a multi-well tray, a microcard, a microslide, a capillary, an etched channel plate, a molded channel plate, an embossed channel plate, etc. The sample chamber can be part of a combination of multiple sample chambers grouped into a row, an array, an assembly, etc. Multi-chamber arrays can include 12, 24, 36, 48, 96, 192, 384, or more, sample chambers. The sample chamber can be shaped to a multi-well tray under the SBS microtiter format.

The term "sample" as used herein refers to any biological or chemical substance in solution with components that can be excited by excitation light to emit fluorescent light. The sample can include one or more nucleic acid sequences to be amplified and/or sequenced. The sample can include reactants for polymerase chain reaction (PCR) and other reactions such as ligase chain reaction, antibody binding reaction, oligonucleotide ligations assay, and hybridization assay. The sample can be subjected to thermal cycling.

The term "dye" as used herein refers to fluorescent dyes can be used to provide different colors depending on the dyes used. Several dyes will be apparent to one skilled in the art of dye chemistry. One or more colors can be collect for each dye to provide identification of the dye or dyes detected. The dye can be a dye-labeled fragment of nucleotides. The dye can be marker triggered by a fragment of nucleotides. The dye can provide identification of components of the sample by association, for example, bonding to or reacting with a detectable marker, for example, a respective dye and quencher pair. The respective identifiable component can be positively identified by the fluorescence of the dye. The dye can be normally quenched, that can become unquenched in the presence of a particular target component in the sample. The fluorescent dyes can be selected to exhibit respective and, for example, different, excitation and emission wavelength ranges. The dye can be measured to quantitate the components. The dye can be detected in real-time to provide information about the identifiable components throughout the reaction. Examples of dye with desirable excitation and emission wavelengths can include 5-FAM™, TET™, and VIC™. The present teaching apply to red dyes, green dyes, and blue dyes.

According to various embodiments, as illustrated in FIGS. 1-5, fluorescent detection system 570 can include sample chamber 568 adapted to receive sample 580 containing one or more fluorescent-light emitting components, for example, fluorescent dyes. The system can include excitation light source 564, and detector 562 for detecting fluorescent light emitted from the samples 580. According to various embodiments, as illustrated in FIG. 1, fluorescent detection system 570 can include, light pipe 24, lens 14, and/or excitation light source 566.

Figure 6A:
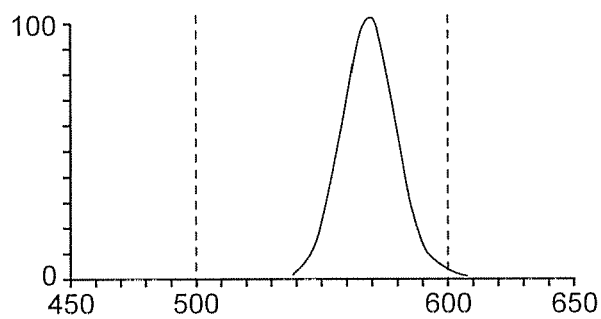
FIGS. 6a-6e illustrate graphs showing the excitation and emission wavelengths and corresponding signal strengths of two dyes, and the wavelength of a filter according to various embodiments.
Figure 6B:
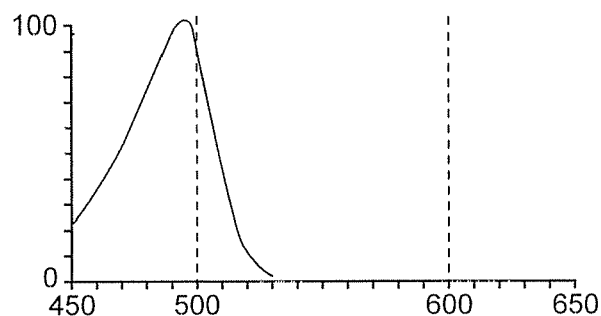
Figure 6C:
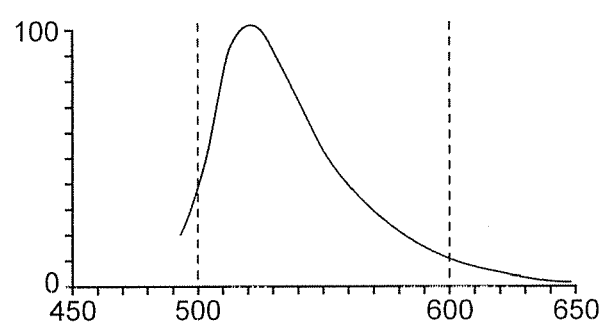
Figure 6D:
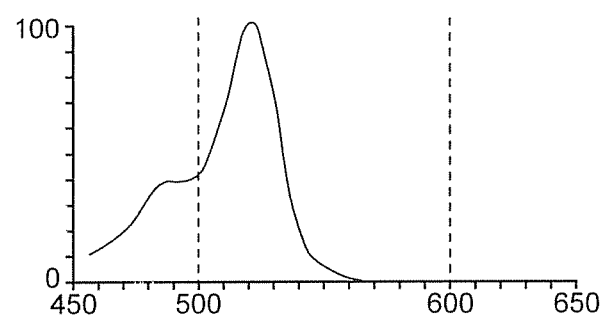
Figure 6E:
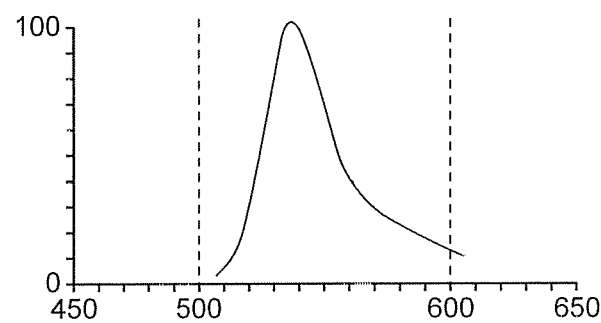

According to various embodiments, as illustrated in FIGS. 6a-6e, the presence of various dyes in a sample utilizing respective excitation wavelength ranges can be used to identify various components. The fluorescent dyes can be chosen such that each dye possesses (a) a discrete or substantially discrete optimum excitation wavelength range, and (b) an emission wavelength range that overlaps with an emission wavelength range of one or more of the other fluorescent dyes. For example, the excitation and emission wavelengths of exemplary dye 5-FAM™ are depicted in FIGS. 6b and 6c, respectively, and the excitation and emission wavelengths of exemplary dye TET™ are depicted in FIGS. 6d and 6e, respectively. As shown, 5-FAM™ and TET™ possess substantially discrete excitation wavelength ranges centered at 470 nm (FIG. 6b) and 525 nm (FIG. 6d), respectively. As shown, the wavelength range of approximately greater than 600 nm, 5-FAM™ (FIG. 6c) and TET™ (FIG. 6e) possess substantially overlapping emission wavelengths. According to various embodiments, as illustrated in FIG. 6a, a filter with an acceptance wavelength range as illustrated in FIG. 6a can substantially reject the excitation wavelengths as illustrated FIGS. 6b and 6d and substantially accept the emission wavelengths as illustrated FIGS. 6c and 6e.

Figure 2:
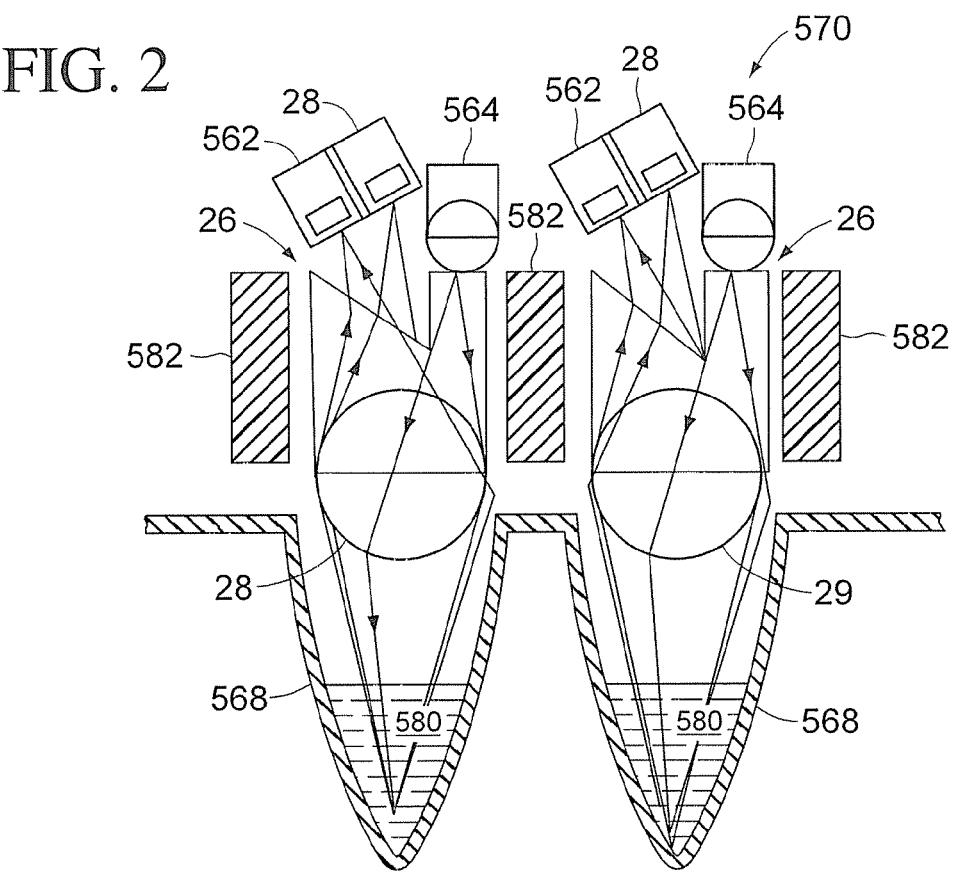
Figure 3:
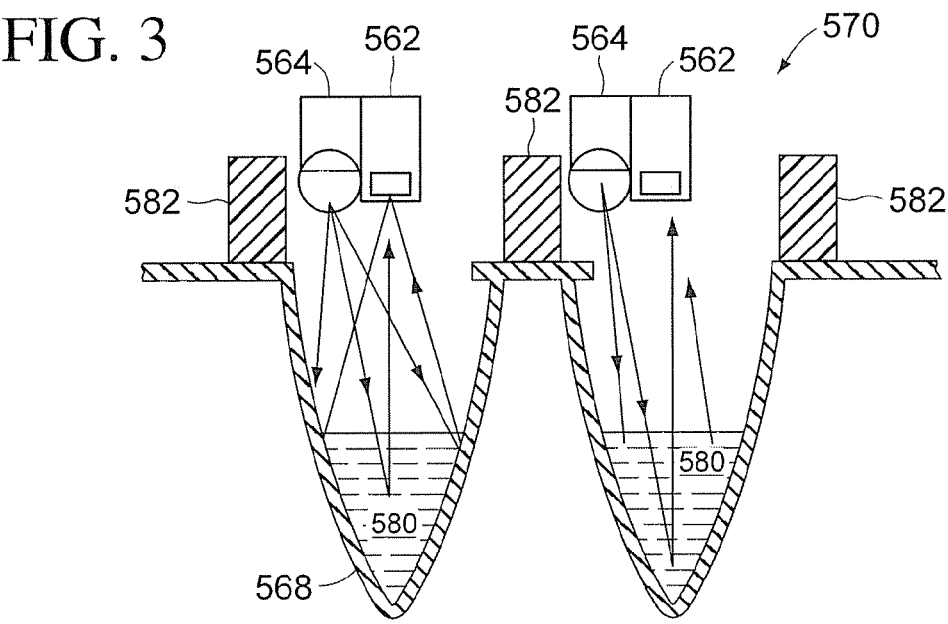
Figure 5:
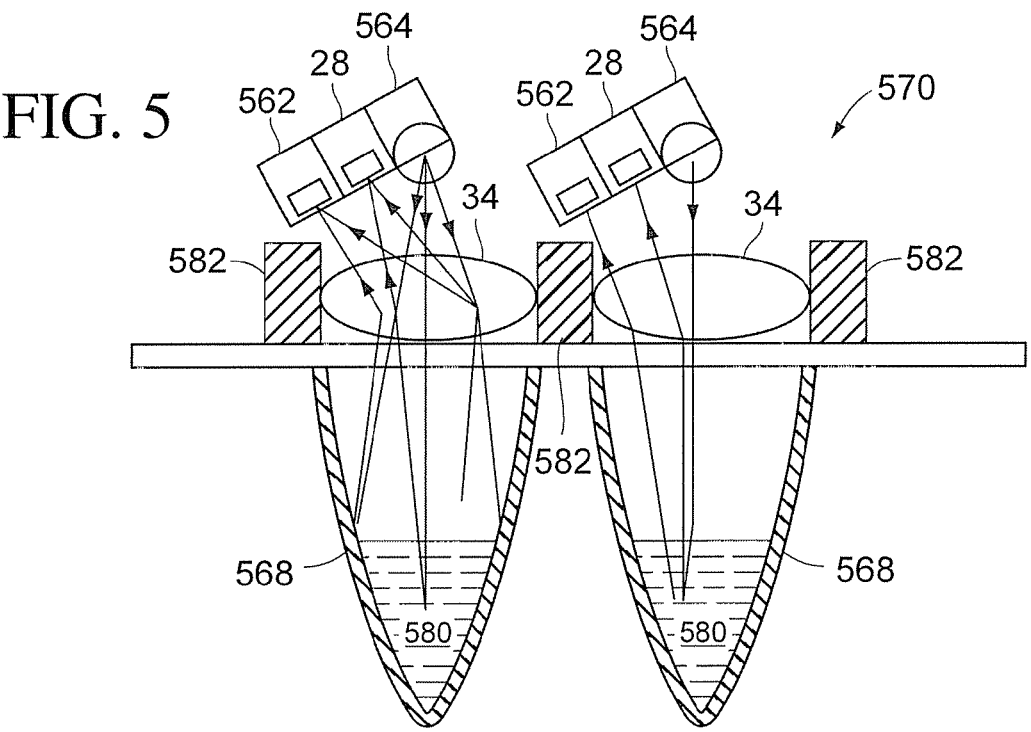

According to various embodiments, as illustrated in FIGS. 2 and 5, fluorescent light detection system 570 can include secondary detector 28 can be provided. Detector 28 can be set to receive, a respective range of wavelengths of fluorescent light different than those of detector 562. According to various embodiments, detectors 562 and 28 can be arranged as an array. According to various embodiments, an array of transmission grating beam splitters can be provided to diffract the fluorescent light into a first component detectable by detector 562 and a second component detectable by detector 28.

Figure 4:
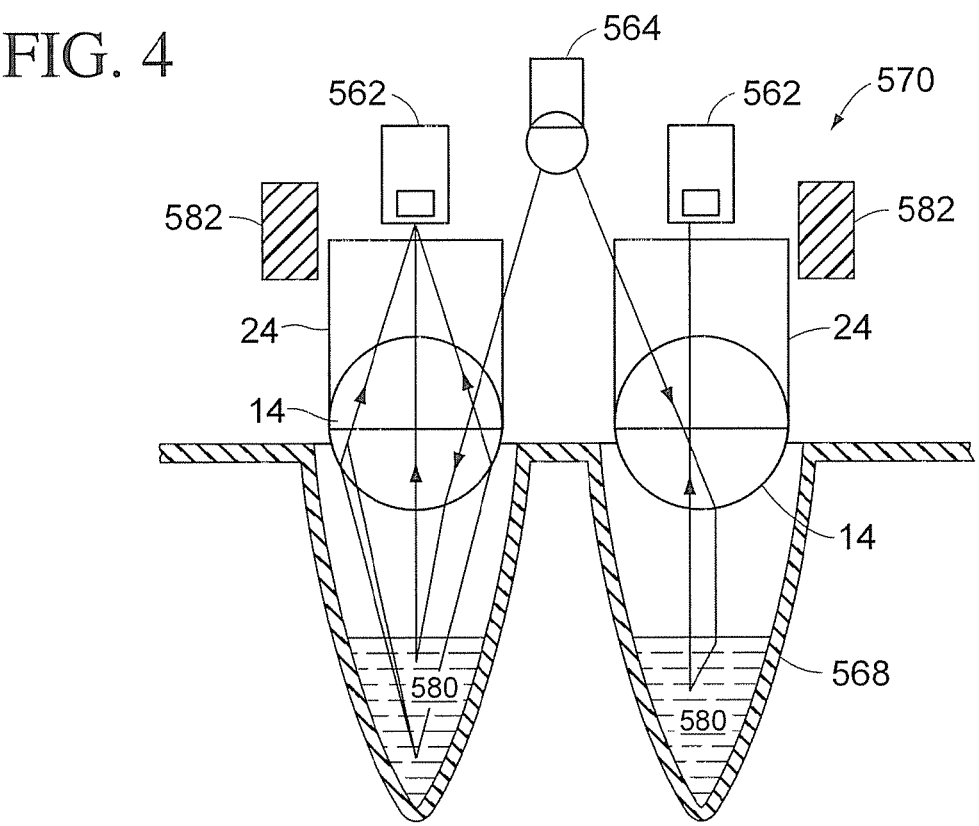

According to various embodiments, as illustrated in FIGS. 1 and 4, lens 14 can focus excitation light into the sample and fluorescent light emitted from the sample. The lens can be any suitable lens configuration, including one or more lenses. The lens can be any lens known to practitioners in the art, for example, a Fresnel lens. According to various embodiments, as illustrated in FIG. 2, prism 26 can be used in conjunction with lens 29. Prism 26 can direct excitation light into sample 580, and lens 29 can focus the fluorescent light emitted by sample 580 into detector 562 and/or detector 28. According to various embodiments, prism 26 can diffract the fluorescent light into a first component detectable by detector 562 and a second component detectable by detector 28. According to various embodiments, a prism 26 can be used independently without any additional lenses. According to various embodiments, devices known in the art can be arranged to direct, separate, filter, or focus the excitation light and/or fluorescent light, for example, a prism, a grating, or a mask.

According to various embodiments, excitation light can be generated by two, three, four, or more excitation light sources for each sample chamber. The multiple excitation light sources can be positioned in an array to correspond with an array of sample chambers. Each excitation light source can emit a respective wavelength range of light to cause fluorescence of a different fluorescent dye.

According to various embodiments, as illustrated in FIG. 4, excitation light from excitation light source 564 can be divided between two samples, three samples, four samples, or more, reducing the number of excitation light sources needed per array of sample chambers 568. The excitation light can be divided between two or more sample chambers 568 by any known device, including fiber optics, a flood illumination device, a lens with or without a mask, a beam splitter, or a combination thereof. According to various embodiments, each sample can correspond to one excitation light source and two detectors. According to various embodiments, each sample can correspond to two excitation light sources and one detector.

According to various embodiments, as illustrated in FIGS. 2 and 5, excitation light source 564 can be a broad-spectrum light source, for example, a white light or halogen light. According to various embodiments, the emitted light of the broad-spectrum light source can be separated into distinct wavelengths or wavelength ranges such that one wavelength or wavelength range at a time can be directed toward the sample 580. The excitation light can be divided into distinct wavelengths or wavelength ranges by, prism 26 or diffraction grating 34. The excitation light path for a single wavelength or of a wavelength range can be controlled by diffraction grating 34.

Figure 7A:
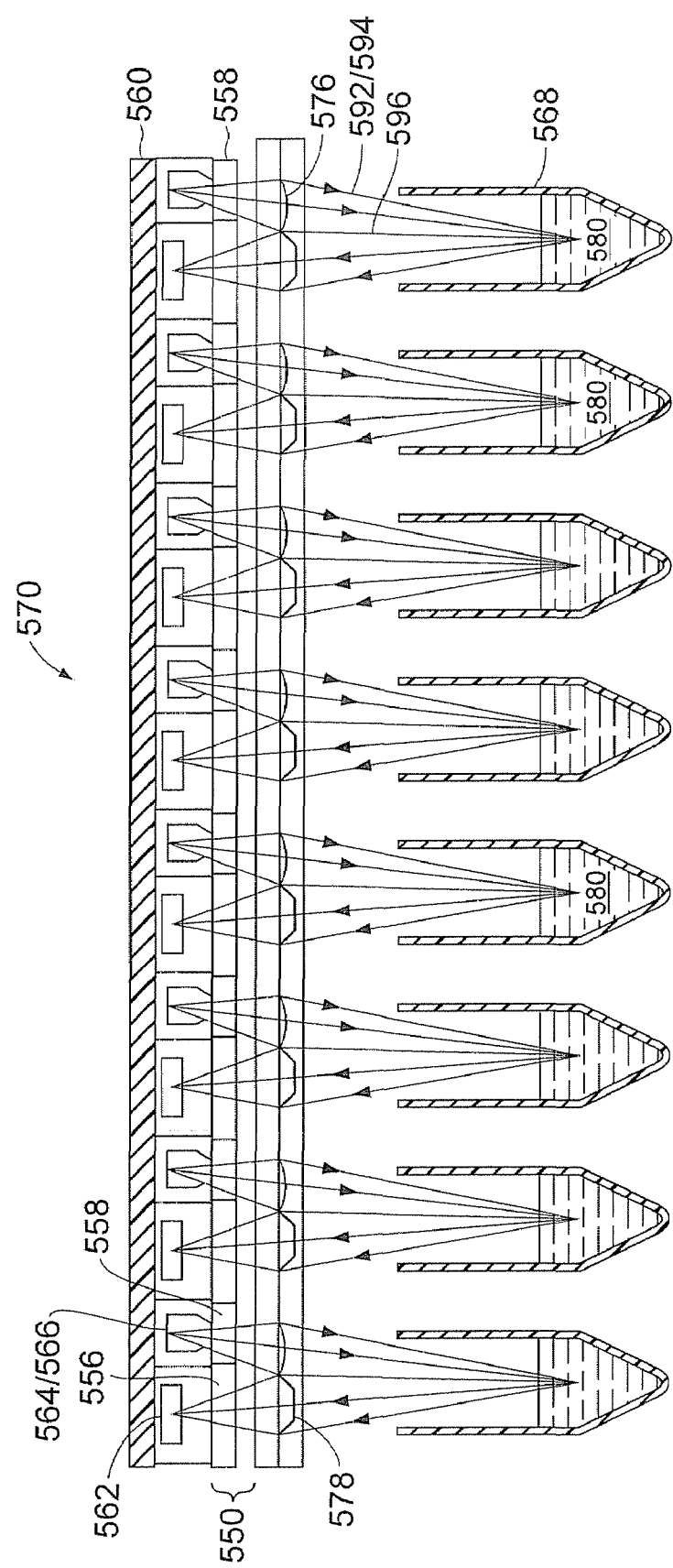
FIG. 7a illustrates a side, partial cross-sectional view of a system according to various embodiments including a filter assembly that includes excitation filters and emission filters.
Figure 9A:
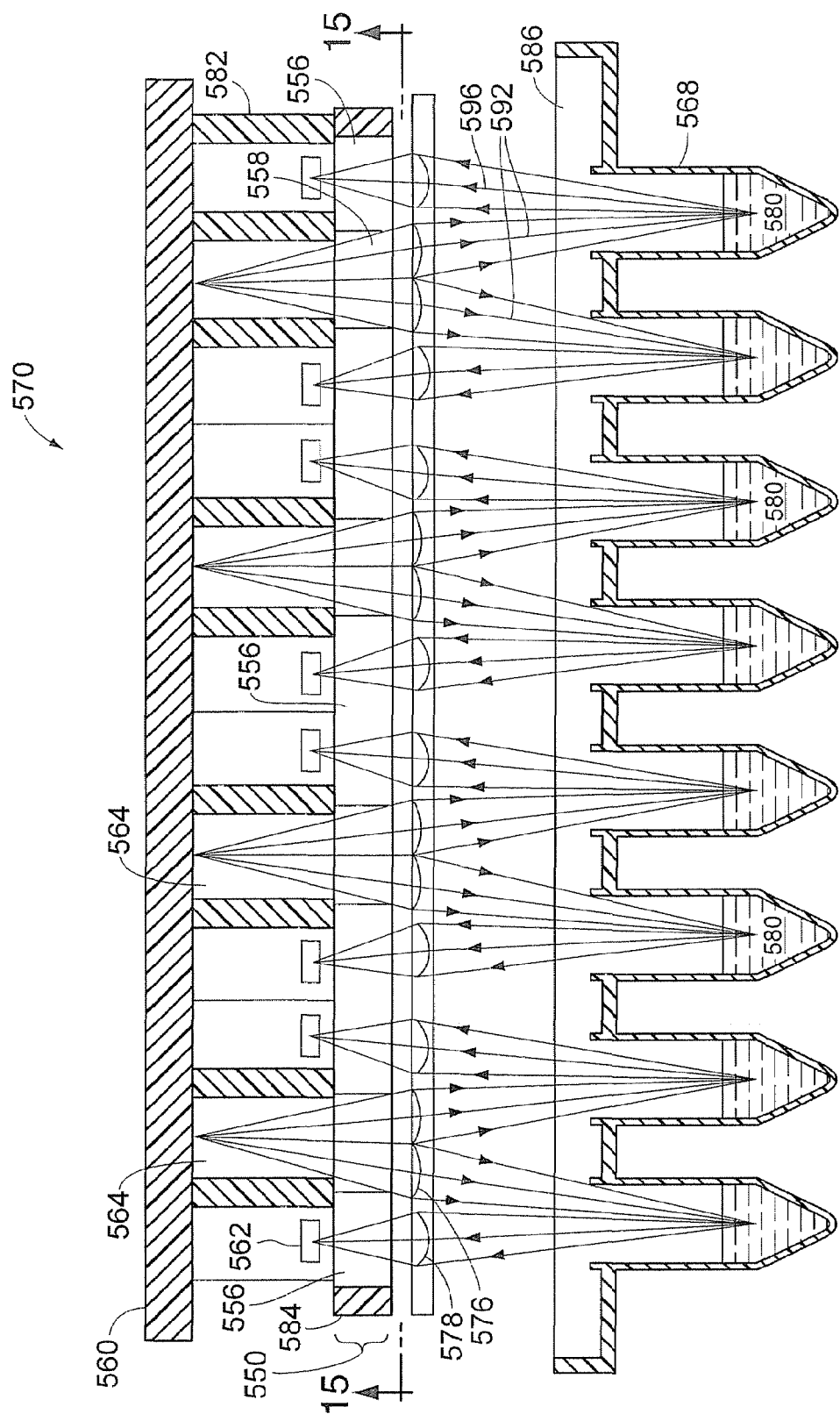
FIG. 9a illustrates a side, partial cross-sectional view of a system according to various embodiments including a filter assembly that includes excitation filters and emission filters.

According to various embodiments, as illustrated in FIGS. 7a and 9a, fluorescent light detection system 570 can include an array of excitation light sources array with a plurality of excitation light sources 564, 566, and a detector array with a plurality of detectors 562. The respective arrays can form a unit of one or more excitation light sources and one or more detectors. According to various embodiments, FIGS. 1-5 and 10 illustrate two units of the array. The excitation light source(s) can be positioned between and/or laterally or longitudinally adjacent to the detector(s) within the array unit. The flat and/or parallel filter assembly is adapted to this lateral or longitudinal positioning of the excitation light sources and detectors.

According to various embodiments, as illustrated in FIGS. 7a-7d, fluorescent light detection system 570 can include filter assembly 550 that can include excitation filter 558 and emission filter 556. Filter assembly 550 can be positioned so that emission filter 558 and emission filter 556 can be located laterally or longitudinally adjacent to excitation light sources 564, 566 and detector 562, respectively. According to various embodiments, excitation filter 558 can be configured to a first wavelength range, and emission filter 556 can be configured to a second wavelength range that differs from the first wavelength range. According to various embodiments, excitation filter 558 can filter out wavelengths up to a maximum wavelength, and emission filter 556 can filter out wavelengths down to a minimum wavelength. According to various embodiments, the first wavelength range can overlap, be spaced-apart, or adjoin the second wavelength range. According to various embodiments, two excitation light sources can be narrow band sources, such as LEDs, and the one detector can be a broad band detector. According to various embodiments, the excitation filter can substantially reject wavelengths outside the first wavelength range those of the narrow band sources. According to various embodiments, the narrow band sources can be aligned with shortpass excitation filters that are adapted to the first wavelength range. According to various embodiments, the emission filter can substantially reject wavelengths in the first wavelength range of the narrow band sources, by being adapted to the second wavelength range. According to various embodiments, the detector can be aligned with longpass emission filters that are adapted to the second wavelength range.

According to various embodiments, a filter assembly can be made of a single substrate or multiple substrates. According to various embodiments, the substrates can be constructed of glass and/or plastic. According to various embodiments, the substrate can be coated to provide regions of excitation filtering and/or emission filtering. According to various embodiments, the substrate can include excitation filters and emission filters laminated together. According to various embodiments, the substrate can be unitary for the fluorescent detection system or portion thereof. According to various embodiments, the substrate can be singular to each sample. According to various embodiments, a filter assembly can be of a unitary construction or can include alternating filter excitation and emission sections. According to various embodiments, the excitation filters and emission filters can be assembled in an overlapping, or interlaced, and/or woven relationship with respect to one another. According to various embodiments, the filters can be multilayered, where either the excitation filter or the emission filter have openings to permit access to the underlying filter. According to various embodiments, the filter assembly can be manufactured either by masking portions of a substrate during coating or by laminating together filter pieces coated separately.

Figure 7B:
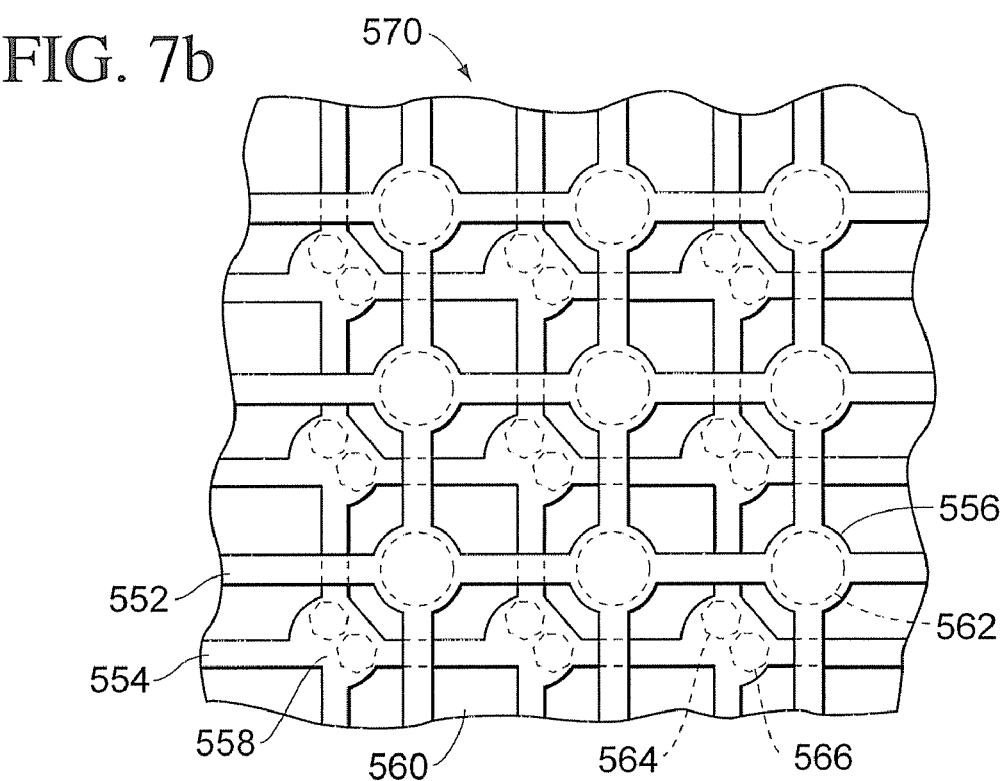
FIG. 7b illustrates a cross-sectional bottom view of a system according to various embodiments showing the overlap of the filter assembly with detectors and excitation light sources.
Figure 7C:
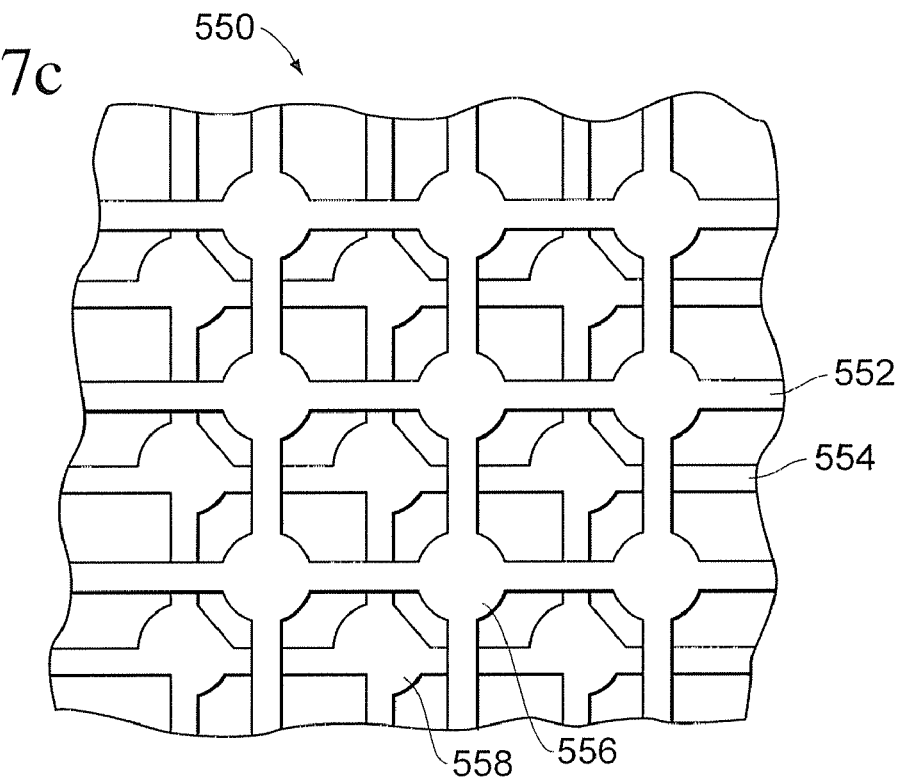
FIG. 7c illustrates a bottom view of the filter assembly according to various embodiments.

According to various embodiments, the filter assembly can include alternating portions of excitation filter and portions of emission filter. According to various embodiments, the alternating portions can be positioned in strips as illustrated in FIGS. 8, 9b, 12a and 12b. According to various embodiments, the alternating portions can be positioned in an staggered array as illustrated in FIGS. 7b and 7c. According to various embodiments, the excitation filter and emission filter can be separate structures coupled together as illustrated in FIGS. 7b and 7c. According to various embodiments, the excitation filter and the emission filter can form a lattice with nodes and openings as illustrated in FIGS. 7b and 7c. According to various embodiments, the excitation filter and the emission filter can be part of one substrate. According to various embodiments, the excitation filter can include a coating on the substrate. According to various embodiments, the emission filter can include a coating on the substrate. According to various embodiments, the substrate can include a first layer configured to provide the excitation filter and a second layer configured to provide the emission filter.

According to various embodiments, the filter assembly can filter a first wavelength range of up to about 565 nanometers (nm), for example from 420 nm to 535 nm, or from 440 nm to 560 nm, with a filtering efficiency of, for example, greater than 70%, greater than 80%, greater than 90%, or 100%, in the first wavelength range. The filter assembly can filter a second wavelength range that can be greater than or equal to, for example, 565 nm, or 580 nm, with a filtering efficiency of, for example, greater than 70%, greater than 80%, greater than 90%, or 100%, in the second wavelength range. According to various embodiments, the maximum wavelength of the first wavelength range can be, for example, 10 nm, 20 nm, 30 nm, 50 nm, or 100 nm, less than the minimum wavelength of the second wavelength range. According to various embodiments, the plurality of excitation light sources can provide excitation light having wavelengths of, for example, 470 nm, 505 nm, 520 nm, 525 nm, 560 nm, 560-580 nm, and/or 620 nm as respective peak wavelengths. According to various embodiments, the plurality of excitation light sources can provide excitation light selected respectively from the red, green, blue, violet, and/or ultra-violet spectra. According to various embodiments, the system can be used with red dyes, green dyes, and blue dyes. According to various embodiments, the excitation filter can have a maximum wavelength of at most 535 nm and the excitation filter can exhibit at least 80% efficiency in rejecting wavelengths greater than the maximum wavelength. According to various embodiments, the emission filter can have a minimum wavelength of at least 535 nm and the excitation filter can exhibit at least about 80% efficiency in rejecting wavelengths less than the minimum wavelength. According to various embodiments, the maximum wavelength of the excitation filter can be 10 nm or more shorter than the minimum wavelength of the emission filter.

According to various embodiments, a fluorescent detection system can include an array of focusing lenses, wherein each of the focusing lenses can be positioned laterally or longitudinally adjacent a respective excitation light source. According to various embodiments, the array of focusing lenses can include a second set of focusing lenses, wherein each of the second set of focusing lenses can be positioned laterally or longitudinally adjacent a respective detector. According to various embodiments, the fluorescent detection system can include an array of collimating lenses, wherein each of the collimating lenses can be positioned laterally or longitudinally adjacent a respective excitation light source. The array of collimating lenses can include a second set of collimating lenses, wherein each of the second set of collimating lenses can be positioned laterally or longitudinally adjacent a respective detector. According to various embodiments, the fluorescent detection system can include an excitation light source array capable of radiating heat.

According to various embodiments, the fluorescent detection system can include an array of focusing lenses. According to various embodiments, each focusing lens can correspond to each sample. According to various embodiments, a first set of focusing lenses can correspond to the excitation light and a second set of the focusing lenses can correspond to the fluorescent light. According to various embodiments, the fluorescent detection system can include an array of collimating lenses. According to various embodiments, the array of collimating lenses can include a first set of collimating lenses for the excitation light and a second set of collimating lenses for the fluorescent light.

According to various embodiments, a fluorescent detection system can include a sample chamber, wherein the sample chamber is a multi-well tray including a plurality of wells. The fluorescent detection system can include an array of excitation light sources including a plurality of excitation light sources, and an array of detectors including a plurality of detectors, wherein at least one of the plurality of the excitation light sources can be positioned laterally or longitudinally adjacent to at least one of the detectors together forming a unit as described herein. The unit can be operatively aligned to direct excitation light toward to detect fluorescent light from at least one of the plurality of wells. According to various embodiments, a control device can be provided to activate at least one of the units. According to various embodiments, as illustrated in FIGS. 1-5 and 10, cross-talk between the excitation light and fluorescent light from each unit can be substantially reduced by using mask 582. The mask can include a mask, masking elements, or a masking layer. According to various embodiments, each unit can include a cover on the well capable of operating as a collimating lens.

According to various embodiments, the filter assembly can provide a first filter region that filters a first wavelength range or up to a maximum wavelength, and a second filter region that filters at least a second wavelength range or down to a minimum wavelength. The maximum wavelength and the minimum wavelength can be the same or different. According to various embodiments, the filter assembly can include alternating filter regions, positioned in an abutting relationship with one another. According to various embodiments, the filter assembly can be shaped as a rectangle having a width and a length. According to various embodiments, the width can be any suitable size, for example, from 50 mm to 125 mm. The length can be any suitable size, for example, from 100 mm to 200 mm. According to various embodiments, each first filter region can have a width from four mm to eight mm. Each second filter region can have a width of from four mm to eight mm.

According to various embodiments, a method of fluorescent detection can include providing a fluorescent detection system including an array of excitation light sources, an array of detectors. Each excitation light source or sets of excitation light sources can be arranged laterally or longitudinally adjacent respective detectors. The method can include generating excitation light detecting fluorescent light emitted from each sample. According to various embodiments, the method can include focusing the excitation light. According to various embodiments, the method can include dividing the excitation light between two or more spaced-apart samples. According to various embodiments, the method can include filtering the excitation light and fluorescent light with a filter assembly. According to various embodiments, the method can include generating a first dataset representative of fluorescent light detected by the detectors. The method can include processing the first dataset with a processor.

According to various embodiments, the arrays of detectors excitation light sources can be positioned on or in a single body, for example, a substrate or a printed circuit board (PCB). According to various embodiments, the PCB can be shaped to correspond to the sample chamber.

According to various embodiments, the sample chamber can be a 96-well microtiter tray utilized for holding or storing multiple samples. A similarly shaped PCB with 96 detectors can be utilized for one-to-one fluorescent detection. According to various embodiments, the detectors can be positioned such that the path of fluorescent light from a sample to a corresponding detector does not intersect the path of fluorescent light from another sample to another detectors. According to various embodiments, one, two, three, four, or more detectors per sample can be utilized. According to various embodiments, one detector can receive fluorescent light from a plurality of samples, for example, from two, three, four, five, or six or more wells in the sample chamber. According to various embodiments, an excitation light source can direct excitation light to a plurality of samples, for example, to two, three, four, five, or six or more wells in the sample chamber.

According to various embodiments, a sample chamber is a 96-well microtiter tray for holding or storing multiple samples. A similarly shaped PCB with 192 individual excitation light sources, can be utilized for excitation. For example, a set of two excitation light sources can be used to illuminate each sample in each well.

According to various embodiments, a filter assembly can be provided that includes a shortpass excitation filter and a longpass emission filter.

According to various embodiments, as illustrated in FIGS. 7a-7d, fluorescent detection system 570 can include filter assembly 550 with excitation filters 558 and emission filter 556. Detectors 562 and excitation light sources 564 and 566 can be positioned on substrate 560. According to various embodiments, focusing lenses 576 and 578, can be aligned with the excitation light sources 564, 566 and detectors 562, respectively, to focus excitation light 592, 594 and fluorescent light 596, respectively.

According to various embodiments, the excitation light sources can be activated simultaneously, individually, or in a pattern.

According to various embodiments, as illustrated in FIGS. 7b and 7c, fluorescent detection system 570 can include filter assembly 550 positioned such that detector 562 can overlap with emission filter 556 and excitation light sources 564, 566 can overlap with excitation filter 558. According to various embodiments, detectors 562 can be a part of a detector array, and can be positioned on substrate 560. According to various embodiments, excitation light sources 564, 566 can be a part of an excitation light source array, and can be positioned on substrate 560.

According to various embodiments, as illustrated in FIG. 7c, filter assembly 550 can include a first filter 556 and a second filter 558. The first filter 556 can include a plurality of emission filters connected by arms 552. The second filter 558 can include a plurality of excitation filters connected by arms 554. Arms 552 and 554 provide the appropriate distancing so that first filters 556 can overlap with detectors 562 and second filters 558 can overlap with excitation light sources 564, 566. According to various embodiments, arms 552 and 554 can provide a nested array of first filter 556 and second filter 558. According to various embodiments, arms 552 and 554 can be woven to assemble first filter 556 and second filter 558 together. According to various embodiments, an adhesive can be positioned at the intersection of arms 552 and 554 to assemble first filter 556 and second filter 558 together. According to various embodiments, filter assembly 550 can be formed using one or more molds, for example, two, three, four, or more molds. According to various embodiments, filter assembly 550 can be made using a first filter mold and a second filter mold. According to various embodiments, the portions of the filters that overlap with the detectors or the excitation light sources can be shaped to align with the shape of the detectors or excitation light sources, for example circular, hexagonal, octagonal, or irregular-geometric shapes. According to various embodiments, adhesive, glue, bonding, tape, notches and inserts, or a rigid border can be used to assembly first filter 554 and second filter 552 into filter assembly 550.

Figure 7D:
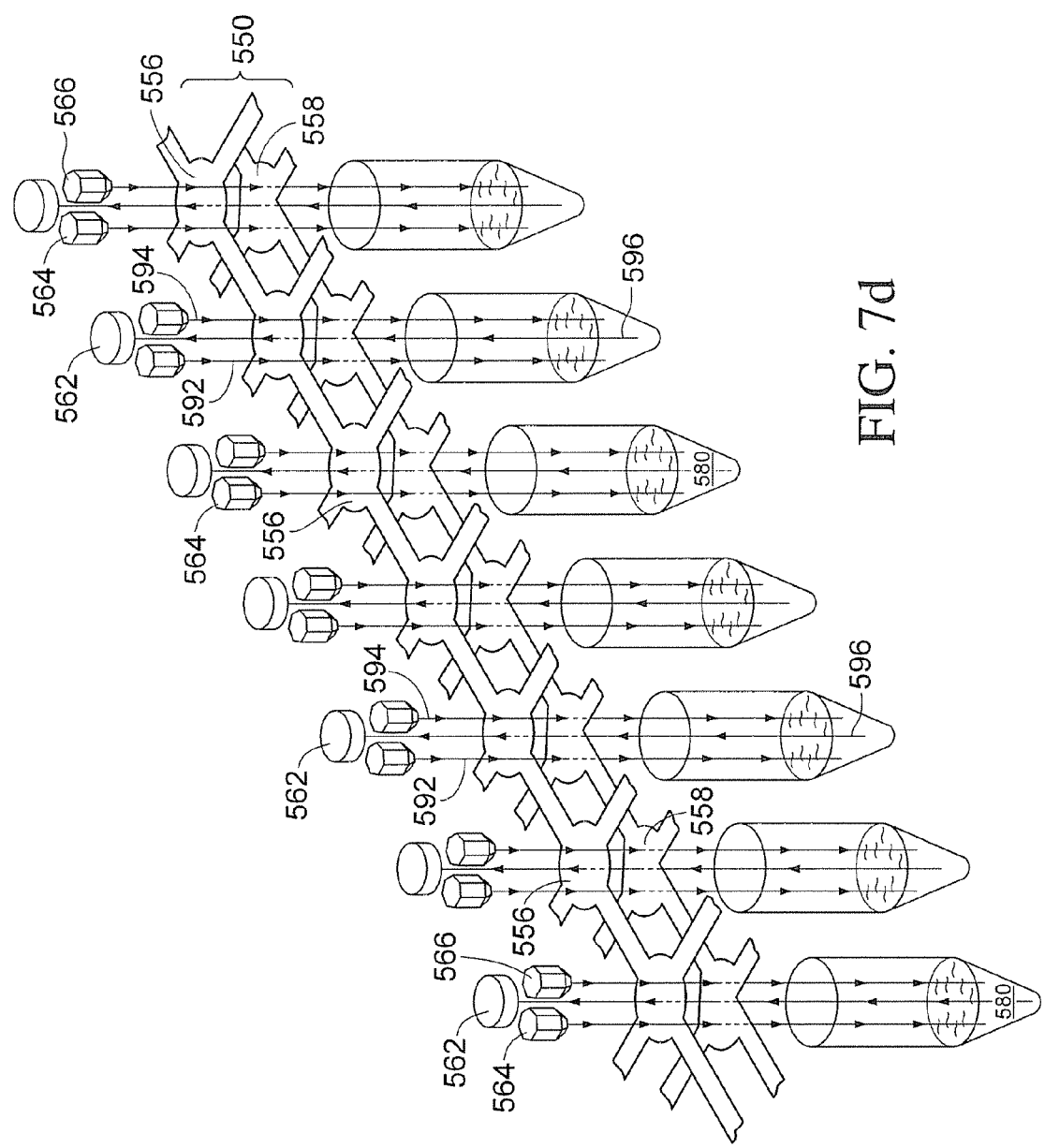
FIG. 7d illustrates a perspective view of a system illustrated in FIG. 7a-b.

According to various embodiments, as illustrated in FIG. 7d, filter assembly 550 can be positioned so that excitation filter 558 overlaps with excitation light sources 564, 566 conditioning excitation light 592, 594 as it travels to sample 580, and emission filter 556 overlaps with detectors 562 conditioning fluorescent light 596 as it travels from sample 580 to detectors 562.

Figure 8:
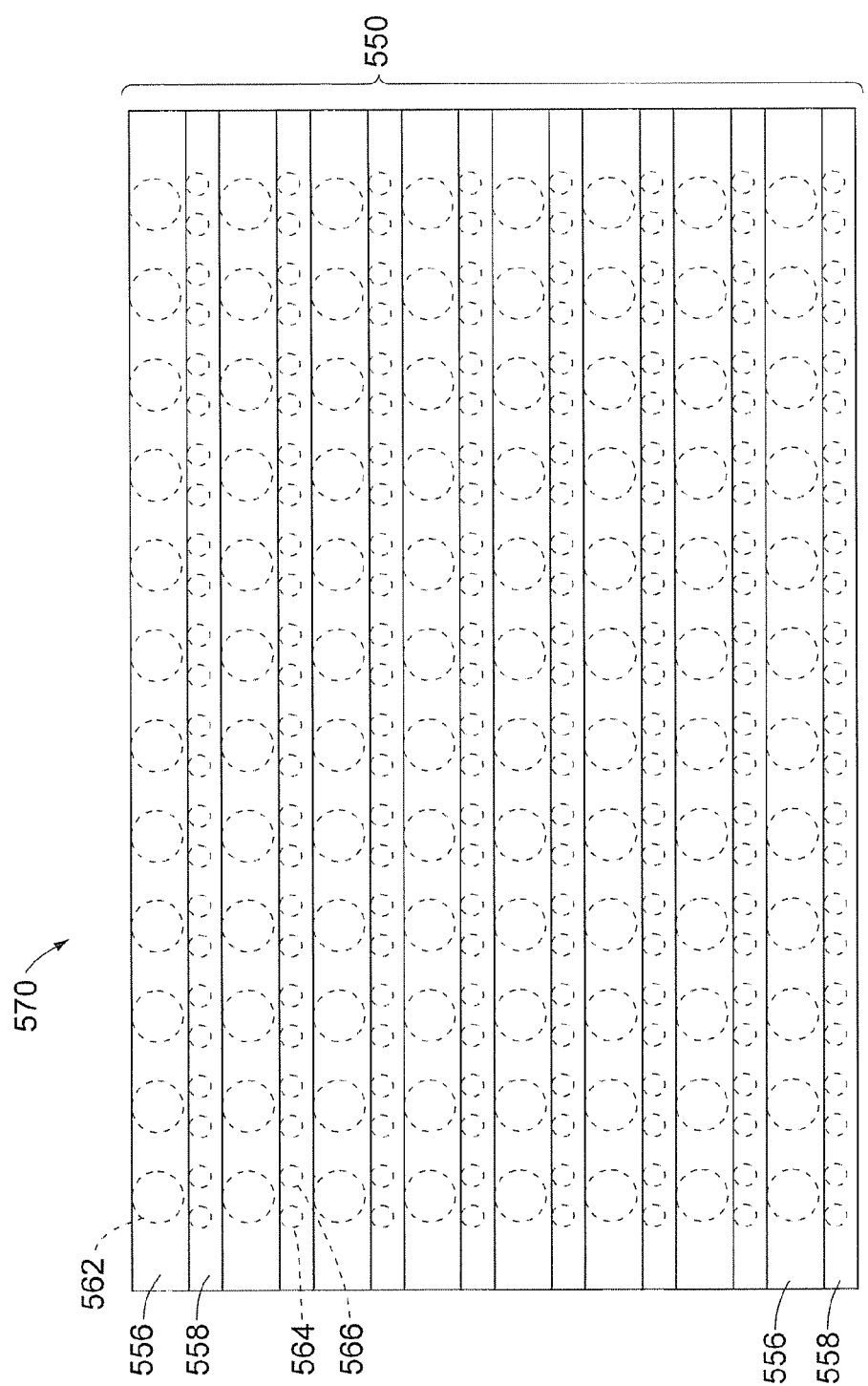
FIG. 8 illustrates a cross-sectional bottom view of a system showing the overlap of the filter assembly with detectors and excitation light sources.

According to various embodiments, as illustrated in FIG. 8, filter assembly 550 can include excitation filters 558 and emission filters 556. Filter assembly 550, as illustrated in FIG. 8, corresponds to a sample chamber with 96 samples, for example, samples in a 96-well tray. According to various embodiments, filters 556 and 558 can be shaped as rectangles, such as strips, positioned in parallel planes or the same plane. According to various embodiments, filters 556 and 558 can have different thicknesses.

According to various embodiments, a filter assembly can be provided that is rectangular in shape and has a width of from 5 mm to 100 mm, for example, a width of 75 mm. The rectangular electromagnetic radiation filter can have a length of from 80 mm to 150 mm, for example, a length of 113 mm. According to various embodiments, filter assembly 550 can be formed by abutting a first filter and a second filter together, with each having the same length, for example, a length of from 80 mm to 150 mm, for example, a length of 111 mm. According to various embodiments, the filters can have a width from 3 mm to 9 mm, for example, a width of 6 mm. According to various embodiments, the filters can be films coated on a substrate. According to various embodiments, the thicknesses of the filters can each be from 0.1 mm to 10 mm thick, for example, 3 mm thick.

According to various embodiments, as illustrated in FIG. 9a, fluorescent detection system 570 can include substrate 560, detectors 562, and excitation light sources 564. Filter assembly 550 can include excitation filter 558 and emission filter 556 positioned laterally or longitudinally adjacent, or in contact with one another. Sleeve 584 can be used to assemble filter assembly 550.

According to various embodiments, as illustrated in FIG. 9a, walls 582 substantially reduce bleach-out of detectors 562 by excitation light 592.

Figure 9B:
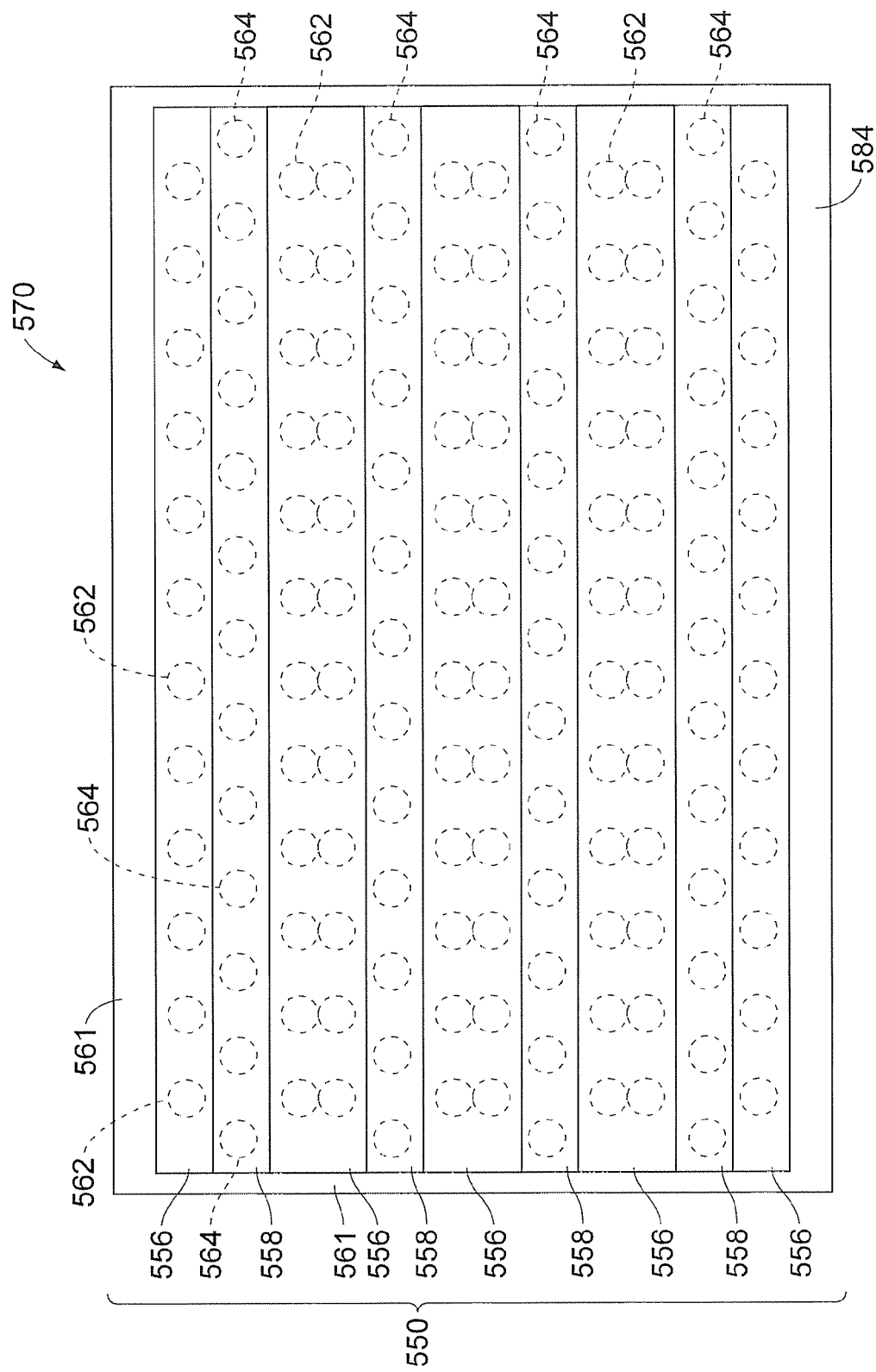
FIG. 9b illustrates a bottom view of the system illustrated in FIG. 9a viewed along line 15-15 showing the overlap of the filter assembly with detectors and excitation light sources.

According to various embodiments, as illustrated in FIG. 9b, filter assembly 550 can be positioned to overlap with detectors 562 and excitation light sources 564. Filter assembly 550 can include excitation filters 558 and emission filters 556. Filter assembly 550, as illustrated in FIG. 9b, corresponds to a sample chamber with 96 samples, for example, samples in a 96-well tray. According to various embodiments, the excitation light sources 564 can be split to provide excitation light, for example, four sample wells (not shown). Sleeve 584 can include frame 561 as well as other components that can house excitation filters 558 and emission filters 556 in filter assembly 550.

According to various embodiments, excitation light sources can provide excitation light more than one different wavelength range. Detectors can be multiplexed such that more than one detector corresponds to each sample. According to various embodiments, a unit with a plurality of detectors and a plurality of samples can be excited by one excitation light source. The fluorescent detection system can be constructed by a plurality of such units as described herein.

Figure 10:
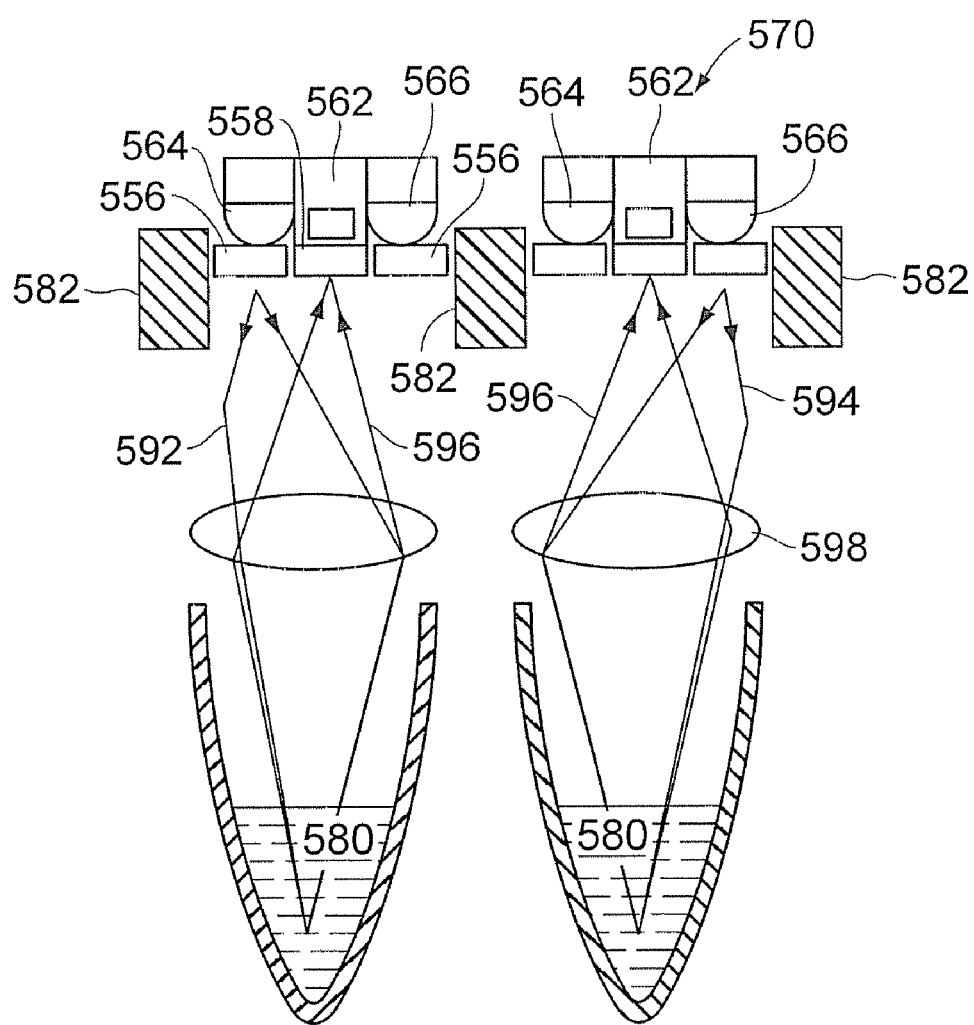
FIG. 10 illustrates a side, partial cross-sectional view of a system according to various embodiments.

According to various embodiments, as illustrated in FIG. 10, a collimating lens 598 can be positioned to direct excitation light 592, 594 to the sample 580 and fluorescent light 596 to detectors 562.

Figure 11A:
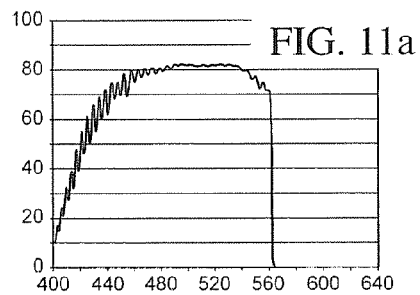
FIG. 11a-11j illustrate a graph showing the excitation and emission wavelengths and corresponding signal strengths of two dyes, and the wavelengths of two filters according to various embodiments.
Figure 11B:
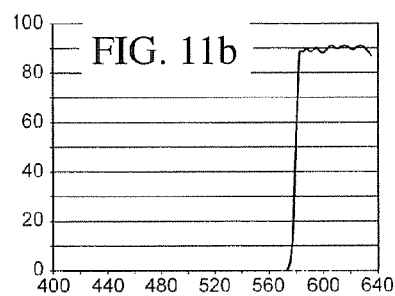
Figure 11C:
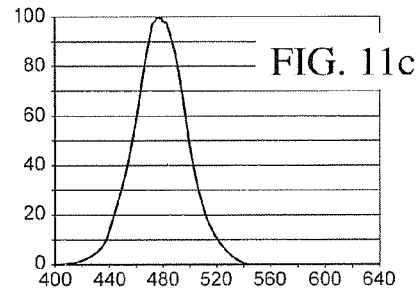
Figure 11D:
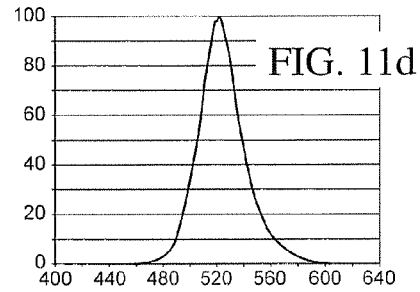
Figure 11E:
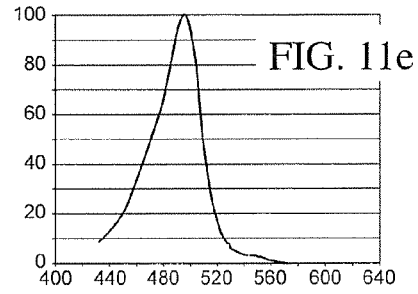
Figure 11F:
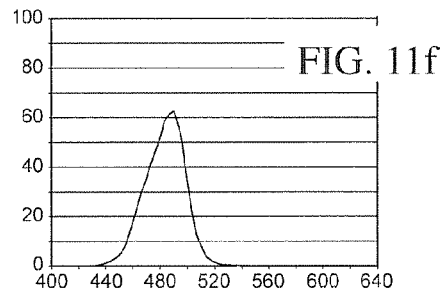
Figure 11G:
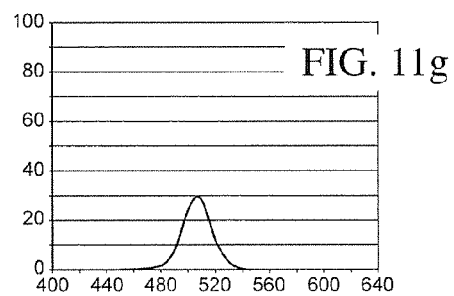
Figure 11H:
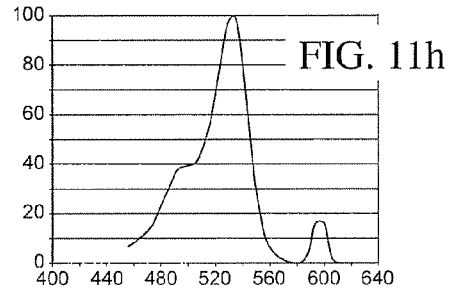
Figure 11I:
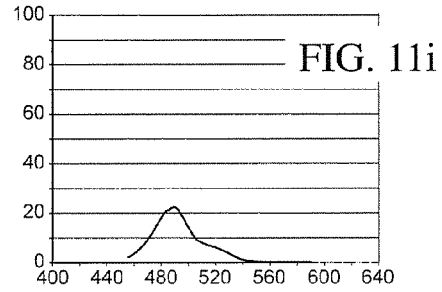
Figure 11J:
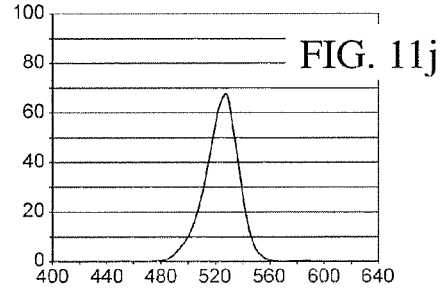

According to various embodiments, as illustrated in FIGS. 11a-11j, excitation light from a blue LED (FIG. 11c), excitation light from a green LED (FIG. 11d), can be substantially accepted by a shortpass filter (FIG. 11a), and substantially rejected by longpass filter (FIG. 11b). The excitation spectrum of FAM dye (FIG. 11e) can be parsed into excitation by the blue LED (FIG. 11f) and excitation by the green LED (FIG. 11g). The excitation spectrum of VIC dye (FIG. 11h) can be parsed into excitation by the blue LED (FIG. 11i) and excitation by the green LED (FIG. 11h). The emission collection by the detectors can be in the range of the longpass filter (FIG. 11b) which substantially rejects the excitation light and substantially accepts emission from both FAM dye and VIC dye based on distinct excitation by the blue LED and green LED.

According to various embodiments, the emission intensities of various dyes in a sample, as detected according to various method embodiments utilizing respective excitation wavelength ranges, can be used to identify various components of the sample. The fluorescent dyes can be chosen such that each dye possesses (a) a discrete or substantially discrete excitation wavelength range, and (b) an emission wavelength range that overlaps with an emission wavelength range of one or more of the other fluorescent dyes. According to various embodiments, yellow LEDs and bluegreen LEDs can be used.

Figure 12A:
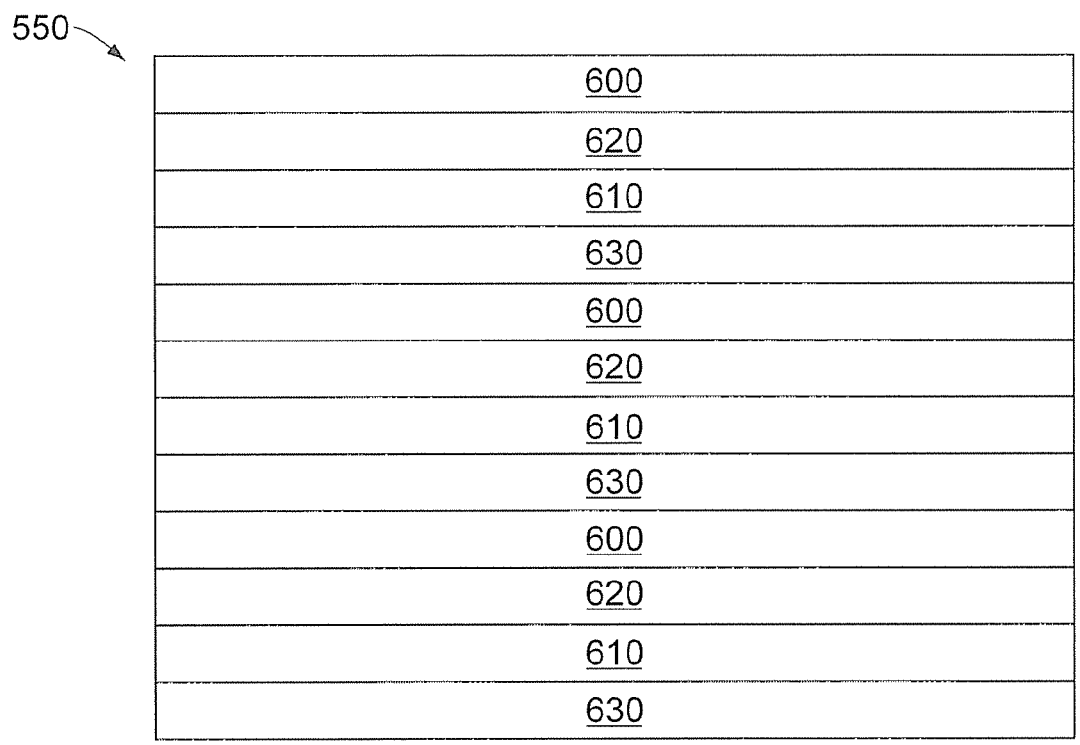
FIGS. 12a-12b illustrate filter assemblies that can include several different excitation and emission filters according to various embodiments.
Figure 12B:
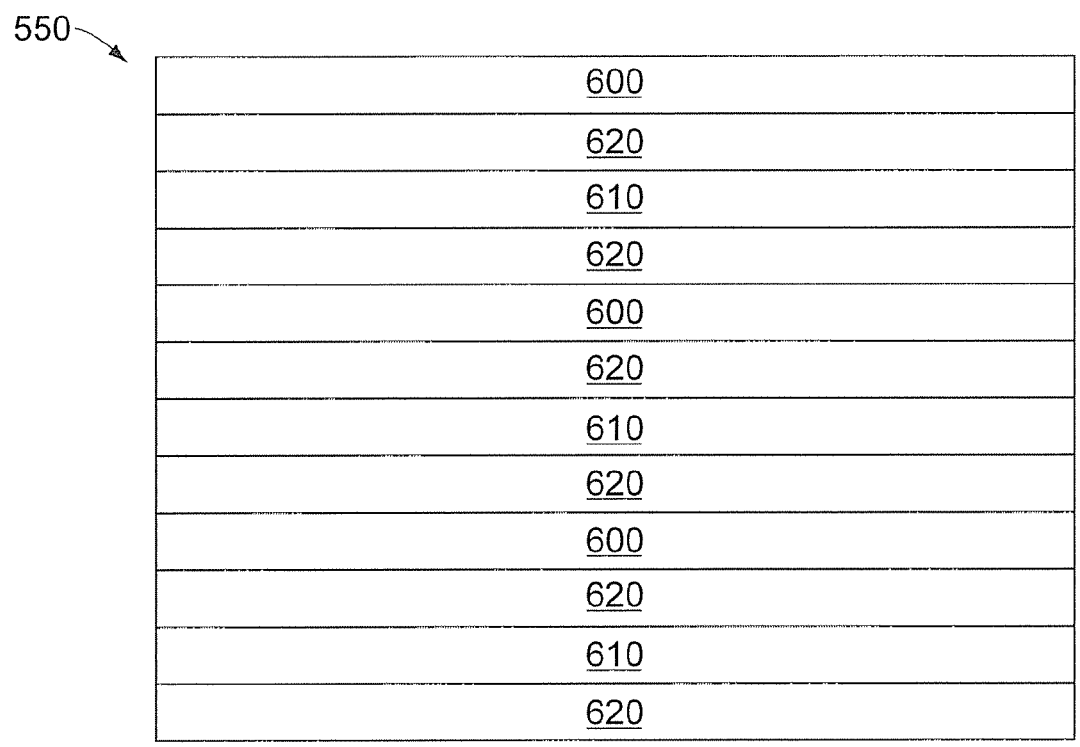

According to various embodiments, filter assembly 550 can include several different excitation filter and emission filters. According to various embodiments, as illustrated in FIG. 12a, filter assembly 550 can include a first excitation filter 600, a first emission filter 610, a second excitation filter 620, and a second emission filter 630. These filters can be alternated to provide an order that is desirable for the configuration of excitation light sources and detectors. According to various embodiments, the first excitation filter can be a shortpass filter, the first emission filter can be shortpass filter, the second excitation filter can be a longpass filter, and the second emission filter can be a longpass filter. According to various embodiments, as illustrated in FIG. 12b, filter assembly 550 can include a first excitation filter 600, an emission filter 610, and a second excitation filter 620. These filters can be alternated to provide an order that is desirable for the configuration of excitation light sources and detectors. According to various embodiments, the first excitation filter can be a shortpass filter, the emission filter can be shortpass filter, and the second excitation filter can be a longpass filter.

According to various embodiments, the present teachings can provide a method of fluorescent detection including providing a flat filter assembly including an excitation filter, and an emission filter, providing excitation light, positioning the excitation light to correspond with the excitation filter, conditioning the excitation light with the excitation filter, providing a sample adapted to generate fluorescent light when excited by the excitation light, positioning the fluorescent light to correspond with the emission filter, conditioning the fluorescent light with the emission filter, detecting the conditioned fluorescent light. According to various embodiments, conditioning the excitation light can include substantially rejecting wavelengths in a wavelength range of the fluorescent light. According to various embodiments, conditioning the emission light includes substantially rejecting wavelengths in a wavelength range of the excitation light. According to various embodiments, positioning the excitation light can include aligning an array of the samples with an array of excitation light sources. According to various embodiments, positioning the fluorescent light can include aligning an array of the samples with an array of detectors.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a light source" includes two or more different light sources. As used herein, the term "include" and its grammatical variants are intended to be non-limiting, such that recitation of items in a list is not to the exclusion of other like items that can be substituted or added to the listed items.

Various embodiments of the teachings are described herein. The teachings are not limited to the specific embodiments described, but encompass equivalent features and methods as known to one of ordinary skill in the art. Other embodiments will be apparent to those skilled in the art from consideration of the present specification and practice of the teachings disclosed herein. It is intended that the present specification and examples be considered as exemplary only.

What is claimed is:

1. A fluorescent detection system comprising:
an array of excitation light sources positioned to correspond to an array of sample chambers, wherein at least two excitation light sources in the array emit a different wavelength range of light to each sample chamber in the array of sample chambers;

an array of detectors positioned to correspond to the array of sample chambers; and a filter assembly comprising an excitation filter positioned for excitation light from the excitation light sources and an emission filter positioned for fluorescent light from the array of samples, wherein the excitation filter and emission filter are positioned substantially parallel to each other.

2. The fluorescent detection system of claim 1, wherein the two excitation light sources are narrow band sources and the one detector is a broad band detector.

3. The fluorescent detection system of claim 2, wherein the excitation filter substantially rejects wavelengths outside those of the narrow band sources.

4. The fluorescent detection system of claim 3, wherein the emission filter substantially rejects wavelengths of the narrow band sources.

5. The analytical instrument of claim 4, wherein the excitation filter has a maximum wavelength of at most 535 nm and the excitation filter exhibits at least 80% efficiency in rejecting wavelengths greater than the maximum wavelength.

6. The analytical instrument of claim 5, wherein the emission filter has a minimum wavelength of at least 535 nm and the excitation filter exhibits at least about 80% efficiency in rejecting wavelengths less than the minimum wavelength.

7. The analytical instrument of claim 6, wherein the maximum wavelength is 10 nm or more shorter than the minimum wavelength.

8. The fluorescent detection system of claim 1, further comprising an array of focusing lenses.

9. The fluorescent detection system of claim 8, wherein each focusing lens corresponds to each sample.

10. The fluorescent detection system of claim 8, wherein a first set of focusing lenses corresponds to the excitation light and a second set of the focusing lenses corresponds to the fluorescent light.

11. The fluorescent detection system of claim 1, further comprising an array of collimating lenses.

12. The fluorescent detection system of claim 11, wherein the array of collimating lenses comprises a first set of collimating lenses for the excitation light and a second set of collimating lenses for the fluorescent light.

13. The fluorescent detection system of claim 1;

wherein the excitation filter and the emission filter form alternating portions of the filter assembly, wherein the filter assembly is substantially flat.

14. The filter assembly of claim 13, wherein the excitation filter and emission filter are separate structures coupled together.

15. The filter assembly of claim 14, wherein the excitation filter and the emission filter form a lattice with nodes and openings.

16. The filter assembly of claim 15, wherein the nodes and openings are positioned in a staggered array.

17. The filter assembly of claim 13, wherein the excitation filter and the emission filter are part of one substrate.

18. The filter assembly of claim 17, wherein the excitation filter comprises a coating on the substrate.

19. The filter assembly of claim 17, wherein the emission filter comprises a coating on the substrate.

20. The filter assembly of claim 17, wherein the substrate comprises a first layer configured to provide the excitation filter and a second layer configured to provide the emission filter.

21. The fluorescent detection system of claim 1, wherein the excitation filter and emission filter are positioned substantially parallel to each other in different parallel planes.

22. The fluorescent detection system of claim 1, wherein the excitation filter and emission filter are positioned substantially parallel to each other in the same plane.

23. A method of fluorescent detection comprising:

providing a filter assembly comprising:

an excitation filter, and an emission filter; wherein the excitation filter and emission filter are positioned substantially parallel to each other;

providing an array of excitation light sources positioned to correspond to an array of sample chambers, wherein at least two excitation light sources in the array emit a different wavelength range of light to each sample chamber in the array of sample chambers;

positioning the excitation light sources to correspond with the excitation filter;

conditioning the excitation light with the excitation filter;

providing a sample in a sample chamber adapted to generate fluorescent light when excited by the excitation light of two or more wavelengths;

positioning the fluorescent light to correspond with the emission filter;

conditioning the fluorescent light with the emission filter;

detecting the conditioned fluorescent light to determine the presence of two or more components in the sample.

24. The method of claim 23, wherein conditioning the excitation light comprises substantially rejecting wavelengths in a wavelength range of the fluorescent light.

25. The method of claim 23, wherein conditioning the emission light comprises substantially rejecting wavelengths in a wavelength range of the excitation light.

26. The method of claim 23, wherein positioning the excitation light comprises aligning an array of the samples with an array of excitation light sources.

27. The method of claim 23, wherein positioning the fluorescent light comprises aligning an array of the samples with an array of detectors.

28. The method of claim 23, wherein the components in the sample are nucleic acid sequences.

* * * * *